United States Patent
Baumbach et al.

(10) Patent No.: US 7,973,279 B2
(45) Date of Patent: Jul. 5, 2011

(54) METHOD AND DEVICE FOR GENERATING POSITIVELY AND/OR NEGATIVELY IONIZED GAS ANALYTES FOR GAS ANALYSIS

(75) Inventors: Joerg Ingo Baumbach, Dortmund (DE); Wolfgang Vautz, Unna (DE); Antje Michels, Dortmund (DE); Joachim Franzke, Dortmund (DE)

(73) Assignee: Leibniz—Institut für Analytische Wissenschaften—ISAS—e.V., Dortmund (DE)

( * ) Notice: Subject to any disclaimer, the term of this patent is extended or adjusted under 35 U.S.C. 154(b) by 292 days.

(21) Appl. No.: 12/311,720

(22) PCT Filed: Sep. 14, 2007

(86) PCT No.: PCT/EP2007/007999
§ 371 (c)(1), (2), (4) Date: Apr. 9, 2009

(87) PCT Pub. No.: WO2008/049488
PCT Pub. Date: May 2, 2008

(65) Prior Publication Data
US 2009/0278038 A1  Nov. 12, 2009

(30) Foreign Application Priority Data
Oct. 25, 2006 (DE) .......................... 10 2006 050 136

(51) Int. Cl.
*H01J 49/26* (2006.01)
*H01J 49/04* (2006.01)
*B01D 59/44* (2006.01)

(52) U.S. Cl. .................. 250/288; 250/290; 250/293
(58) Field of Classification Search .................. 250/281, 250/282, 288, 289, 290, 293, 423 R, 424
See application file for complete search history.

(56) References Cited

U.S. PATENT DOCUMENTS

| 4,549,082 | A  | * | 10/1985 | McMillan ............... 250/423 R |
| 5,746,051 | A  | * | 5/1998  | Kieser et al. .............. 60/275 |
| 5,994,849 | A  | * | 11/1999 | Vollkommer et al. ..... 315/246 |
| 6,207,954 | B1 | * | 3/2001  | Andrien et al. .......... 250/288 |

(Continued)

FOREIGN PATENT DOCUMENTS

GB  2 252 160  7/1992

OTHER PUBLICATIONS

International Search Report.

*Primary Examiner* — Bernard E Souw
(74) *Attorney, Agent, or Firm* — Collard & Roe, P.C.

(57) ABSTRACT

A solution is supposed to be created with a method for generating positively and/or negatively ionized gas analytes for gas analysis in an ion mobility spectrometer or in a mass spectrometer, with which method the gas analyte can be ionized without the restrictions of previous ionization methods for gas analysis in an ion mobility spectrometer or in a mass spectrometer, forming positive and/or negative ions.

Figure 1:
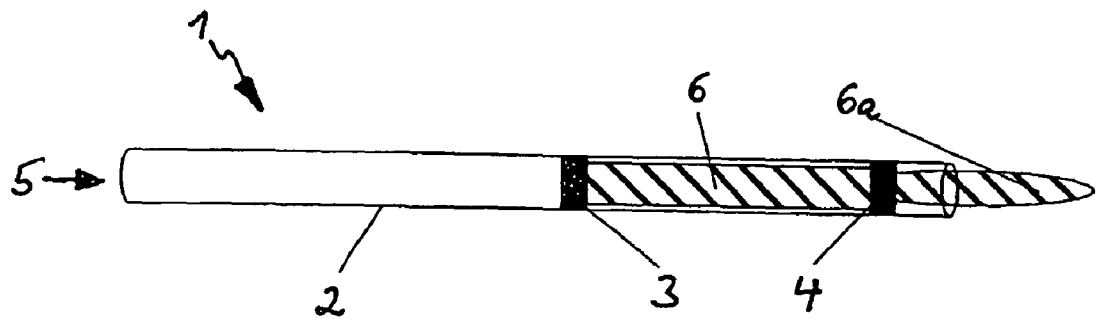

This is achieved in that the positive and/or negative gas ions are generated by means of a plasma, which is brought about by means of a dielectrically inhibited discharge, whereby the dielectrically inhibited discharge is produced in that a noble gas is passed in through a capillary made of a dielectric material, whereby an alternating voltage is applied by means of two electrically insulated electrodes disposed on the capillary adjacent to the exit region of the capillary, and the gas analyte is passed to the exit region outside of the capillary.

9 Claims, 1 Drawing Sheet

U.S. PATENT DOCUMENTS

| | | |
|---|---|---|
| 6,326,616 B1 * | 12/2001 | Andrien et al. ............... 250/288 |
| 6,359,275 B1 | 3/2002 | Bertsch et al. |
| 6,483,255 B1 * | 11/2002 | Vollkommer et al. ........ 315/246 |
| 6,486,469 B1 | 11/2002 | Fischer et al. |
| 6,541,768 B2 * | 4/2003 | Andrien et al. ............... 250/288 |
| 6,573,494 B1 * | 6/2003 | Andrien et al. ............... 250/288 |
| 6,683,659 B2 * | 1/2004 | Dirscherl et al. ............... 349/32 |
| 7,498,592 B2 * | 3/2009 | Hershkowitz et al. ..... 250/492.3 |
| 7,759,643 B2 * | 7/2010 | Lloyd et al. ................... 250/324 |
| 2002/0011561 A1 | 1/2002 | Park |
| 2003/0070913 A1 | 4/2003 | Miller et al. |
| 2009/0294660 A1 * | 12/2009 | Whitehouse et al. ......... 250/288 |

* cited by examiner

METHOD AND DEVICE FOR GENERATING POSITIVELY AND/OR NEGATIVELY IONIZED GAS ANALYTES FOR GAS ANALYSIS

CROSS REFERENCE TO RELATED APPLICATIONS

This application is the National Stage of PCT/EP2007/007999 filed on Sep. 14, 2007, which claims priority under 35 U.S.C. §119 of German Application No. 10 2006 050 136.5 filed on Oct. 25, 2006. The international application under PCT article 21(2) was not published in English.

The invention relates to a method and a device for generating positively and/or negatively ionized gas analytes for gas analysis in an ion mobility spectrometer or in a mass spectrometer.

Ion mobility spectrometry is a method for characterizing gaseous chemical substances by way of their mobility in the gas phase, at atmospheric pressure. A carrier gas transports the analyte molecules into the ionization chamber, where ultraviolet light, beta radiation, or particle discharge are used to ionize the molecules. The ions that form in this way are accelerated in an electrical field, in the direction of the detector. In this connection, they move opposite the flow direction of the drift gas, and collide with the drift gas molecules. This brings about braking of the ions as a function of their mass, shape, and charge. The mobility of the ions is calculated on the basis of the time that the ions require to reach the detector (drift time), and the electrical field intensity, and this mobility can be used to identify an analyte. The determination of the signal area in comparison with a prior calibration furthermore allows a quantitative determination of the detected substance.

Ion mobility spectrometers (IMS) are used for many different types of applications, such as the recognition of chemical weapons, explosives, and drugs. Furthermore, they are used, for example, for process monitoring, for monitoring air quality in indoor spaces, for foods quality and safety, and for early detection of lung diseases. The typical limits of detection for these applications lie in the ng/L to pg/L, i.e. $ppb_v$ to $ppt_v$ range.

To carry out ion mobility spectrometry and also molecule mass spectrometry, it is necessary to ionize the analyte gas. Ionization methods that have been used until now are ultraviolet light, electrical particle discharge, and beta radiation, each of which is connected with various disadvantages:

ultraviolet light: low sensitivity, only positive ions are generated,
electrical particle discharge: low long-term stability,
beta radiation: radioactive radiation, which is not suitable for all application cases, or requires a permit.

Within the scope of the miniaturization of analytical instruments and methods, there is a great interest in miniaturized plasma sources, or plasma sources that can be implemented in a microchip. A highly promising approach to this is dielectrically inhibited discharge, which was already discovered by Siemens in 1857, with regard to ozone production. Such discharges have been used, up to the present, in plasma displays for color monitors, in UV radiation sources and $CO_2$ lasers, for exhaust gas purification, for plasma catalysis of methanol, and for the production of ozone.

It is the task of the invention to create a solution with which a gas analyte can be ionized for gas analysis in an ion mobility spectrometer or in a mass spectrometer, forming positive and/or negative ions, without the restrictions of previous ionization methods.

This task is accomplished, according to the invention, in the case of a method of the type indicated initially, in that the positive and/or negative gas ions are generated by means of a plasma, which is brought about by means of a dielectrically inhibited discharge, whereby the dielectrically inhibited discharge is produced in that a noble gas is passed in through a capillary made of a dielectric material, whereby an alternating voltage is applied by means of two electrically insulated electrodes disposed on the capillary adjacent to the exit region of the capillary, and the gas analyte is passed to the exit region outside of the capillary.

By means of such a miniaturized dielectrically inhibited discharge, it is possible to generate positive and negative gas ions of the gas analyte, without having the restrictions of the previously known ionization methods for ion mobility spectrometers and mass spectrometers. The advantage of the method as compared with a beta radiation as the ionization source lies in being able to do without radioactive material that brings with it a restriction in usability and/or requires a handling permit, while keeping the selectivity and sensitivity the same. The advantage in comparison with UV light as the ionization source is the greater sensitivity and selectivity, in particular, since by means of this plasma ionization, in contrast to UV light, negative ions can also be made available and detected. Since, in the case of an ion mobility spectrometer, the power supply of the plasma can be combined with the high voltage of the drift segment, no additional power supply is furthermore required, as it is for supplying a UV lamp. The advantage in comparison with particle discharge as the ionization source lies in achieving the same sensitivity and selectivity at greater long-term stability. Furthermore, as compared with particle discharge, no additional power supply for the plasma ion source is required, either.

The gas analyte is passed, in usual manner, for example, to the ionization chamber of an ion mobility spectrometer, into which chamber the exit region of the capillary projects. The gas analyte then flows past the capillary on the outside, and is ionized by the plasma.

In this connection, an alternating voltage in the range of 500 V to 5000 V is preferably used, and the dielectrically inhibited discharge is operated at ambient pressure. A plasma is formed between the electrodes and outside of the capillary, as a function of the pressure that is set, the flow between the electrodes, the noble gas that is used (preferably helium or argon), and the location of the mass that is applied. The plasma outside of the capillary represents a plasma torch. The end of the capillary, i.e. its exit region, can be integrated into the ionization chamber of an ion mobility spectrometer, for example, as an ionization source.

Locally resolved spectroscopic emission measurements showed that the locations of maximal excitation are dependent on the gas flow. The higher the gas flow, the farther away the excited atomic states at the end of the capillary. However, no emission lines can be measured more than 2-3 cm outside of the capillary, since the energy is transmitted on the basis of surges. It has been shown that in this discharge, the emission of excited nitrogen molecules is higher than the emission of excited atomic states. It can be assumed that, as in the case of the beta emitter, the positive ionization proceeds by way of protonization, and the negative ionization proceeds by way of electron accumulation. In this way, a combination with ion mobility spectrometers in miniaturized form is also possible, particularly because the plasma can also be operated at atmospheric pressure.

To accomplish the task described above, the invention also provides for a device of the type described initially, which is characterized by a capillary made of a dielectric material, for passing in a noble gas, whereby two electrically insulated electrodes to which alternating voltage is applied are disposed on the capillary, adjacent to the exit region of the capillary.

Preferably, in this connection, the capillary consists of glass and has an inside diameter between 50 and 500 µm. The wall thickness of the capillary lies on the order of 350 µm.

In this connection, the electrodes, which are spaced apart from one another in the longitudinal direction of the capillaries, are preferably disposed at a maximal distance of 1 cm. The capillaries and the electrodes can preferably be integrated into a mantling composed of an electrically insulating material.

Preferably, the device is used in an ion mobility spectrometer, whereby the exit region of the capillary extends radially or axially into the ionization chamber of the ion mobility spectrometer, depending on the requirements and the construction of the ion mobility spectrometer.

Furthermore, the device is preferably used in a (molecule) mass spectrometer.

Figure 2:
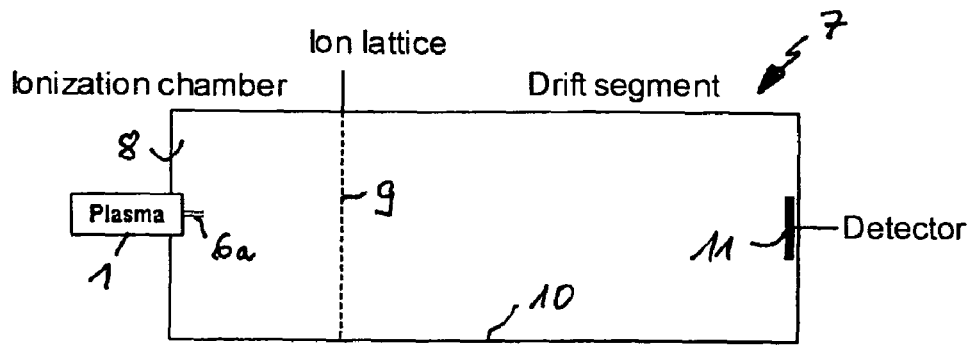
Figure 3:
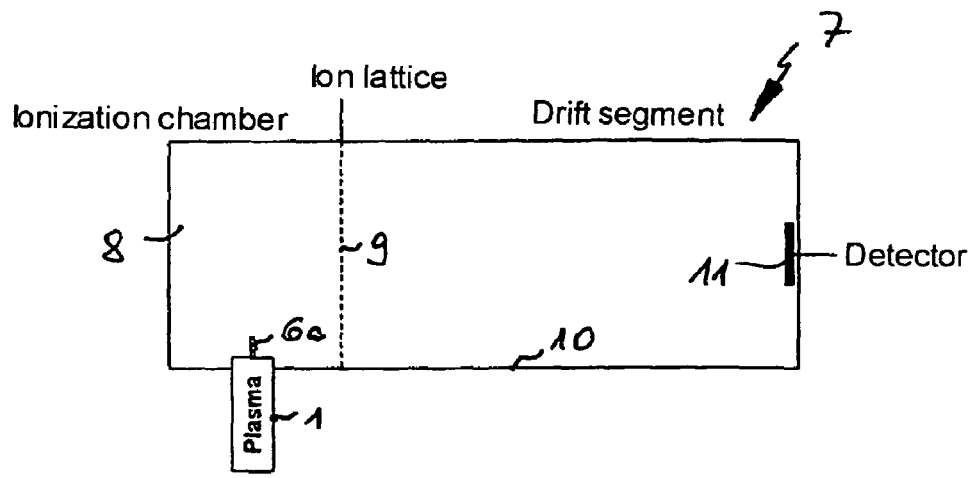

The invention will be explained in greater detail below, using the drawing as an example. This drawing shows, in:

FIG. 1 a schematic, enlarged representation of a device according to the invention, FIG. 2 a fundamental diagram of an ion mobility spectrometer having a device according to the invention in a first installation situation, and FIG. 3 an ion mobility spectrometer having a device according to the invention in a second installation situation.

A device for generating positively and/or negatively ionized gas analytes for gas analysis in an ion mobility spectrometer or mass spectrometer is referred to, in general, with 1 in FIG. 1. This device 1 has a capillary 2 that preferably consists of glass and has an inside diameter between 50 to 500 µm at a wall thickness of about 350 µm. In the frontal exit region of this capillary 2, two ring-shaped electrodes 3, 4, for example, are disposed, spaced apart from one another in the longitudinal direction of the capillary 2, which electrodes surround the capillary 2 on the outside. The distance between the electrodes 3, 4 amounts to maximally about 1 cm. The capillary 2 and the electrodes 3, 4 are preferably embedded in an electrically insulating mantling, not shown.

A noble gas, preferably helium or argon, is passed in through the capillary 2, in the direction of the arrow 5. An alternative voltage between 500 and 5000 V is applied to the electrodes 3, 4, so that a plasma 6 forms between the electrodes 3, 4 and outside of the exit region of the capillary 2, as a function of the pressure that is set, the flow between the electrodes 3, 4, the noble gas that is used, and the location of the applied mass. The plasma 6 outside of the exit region of the capillary 2 represents a plasma torch 6a. The gas analyte is passed to the exit region of the capillary 2 outside of the capillary 2, i.e. flows past this region and is ionized when this happens.

Such a device 1 can be used as an ionization source for an ion mobility spectrometer.

Such an ion mobility spectrometer is shown schematically in FIGS. 2 and 3, and referred to, in general, with 7. This ion mobility spectrometer 7 has an ionization chamber 8, an ion lattice 9, a drift segment 10, and, at the end of the drift segment 10 (i.e. of the drift chamber), a detector 11. The gas analyte is passed to the ionization chamber 8 through a gas inlet, not shown; the gas analyte flows past the exit region of the capillary 2, i.e. past the plasma torch 6a, from the outside, and is ionized.

In the embodiment according to FIG. 2, the device 1 is disposed axially in the ionization chamber of the ion mobility spectrometer 7, as an ionization source.

As FIG. 3 shows, the arrangement can also, alternatively, be made so that the device 1 is disposed radially in the ionization chamber 8.

The gas analyte that is passed in by means of a carrier gas or the like, through the gas inlet, and is to be analyzed, is ionized in the ionization chamber 8 of the ion mobility spectrometer 7, into positive and/or negative analyte ions by means of the device 1, i.e. the plasma that is formed there. In this connection, ionization preferably takes place at atmospheric pressure.

The device 1 can be used not only for gas analysis in an ion mobility spectrometer 7, but also in a (molecule) mass spectrometer, which is not shown in the drawing; then, the placement of the device 1 on the (molecule) mass spectrometer is structured in similar manner as in the case of an ion mobility spectrometer.

The invention claimed is:

1. Method for generating at least one of positively ionized gas analytes and negatively ionized gas analytes for gas analysis in an ion mobility spectrometer or in a mass spectrometer,
   wherein
   the at least one of positive gas ions and negative gas ions are generated by means of a plasma, which is brought about by means of a dielectrically inhibited discharge, whereby the dielectrically inhibited discharge is produced in that a noble gas is passed in through a capillary made of a dielectric material, whereby an alternating voltage is applied by means of two electrically insulated electrodes disposed on the capillary adjacent to the exit region of the capillary, and the gas analyte is passed to the exit region outside of the capillary.

2. Method according to claim 1, wherein
   an alternating voltage in the range of 500 V to 5000 V is used.

3. Method according to claim 1, wherein
   the dielectrically inhibited discharge is operated at ambient pressure.

4. Device for generating at least one of positively ionized gas analytes and negatively ionized gas analytes for gas analysis in an ion mobility spectrometer or in a mass spectrometer, for carrying out the method according to claim 1, wherein
   a capillary (2) made of a dielectric material, for passing in a noble gas, whereby two electrically insulated electrodes (3, 4) to which alternating voltage is applied are disposed on the capillary (2), adjacent to the exit region of the capillary (2).

5. Device according to claim 4, wherein
   the capillary (2) consists of glass.

6. Device according to claim 5, wherein
   the capillary (2) has a diameter between 50 and 500 µm.

7. Device according to claim 4, wherein
   the electrodes (3, 4), which are spaced apart from one another in the longitudinal direction of the capillary, are disposed at a maximal distance of 1 cm.

8. Use of a device according to claim 4 in an ion mobility spectrometer, whereby the exit region of the capillary (2) extends into the ionization chamber of the ion mobility spectrometer.

9. Use of a device according to claim 4 in a mass spectrometer.

* * * * *